United States Patent [19]

Mayeaux

[11] 4,254,797

[45] Mar. 10, 1981

[54] APPARATUS FOR PRODUCING CALIBRATION GASES SUITABLE FOR ANALYTICAL INSTRUMENTATION

[75] Inventor: Paul H. Mayeaux, Houston, Tex.

[73] Assignee: Bi-M Instrument Company, Houston, Tex.

[21] Appl. No.: 6,664

[22] Filed: Jan. 26, 1979

[51] Int. Cl.³ .................. G05D 7/06; G01M 27/00
[52] U.S. Cl. .................................. 137/565; 137/557; 137/625.12; 364/558; 364/571
[58] Field of Search ................ 137/88, 3, 606, 607, 137/565, 625.12

[56] References Cited

U.S. PATENT DOCUMENTS

| 3,335,755 | 8/1967 | Harris et al. | 137/607 X |
| 3,653,842 | 4/1972 | Putman | 137/88 X |
| 3,780,761 | 12/1973 | Whitson et al. | 137/565 |
| 3,934,462 | 1/1976 | Rende | 364/558 X |
| 3,948,281 | 4/1976 | Strain et al. | 137/93 |
| 4,085,766 | 4/1978 | Weigl et al. | 137/88 |
| 4,142,860 | 3/1979 | Mayeaux | 73/1 G X |

Primary Examiner—Daniel M. Yasich
Attorney, Agent, or Firm—Llewellyn A. Proctor

[57] ABSTRACT

Apparatus, useful for blending predetermined accurately measured quantities of gaseous components transferred from separate pressurized supply tanks to a gas blending system, preferably on input signals received from a computer. The gas blending system includes a mixing vessel, a pressure transducer associated with said vessel for measuring the pressure of the gases, and producing an output signal and transmitting same to the computer, a circulating pump connected in series via conduits which form a circuit, and valves; preferably a multi-component valve assembly operatively communicating the two ends of the conduits for flow of gas therethrough in providing the functions of purging gas from the system, evacuating the system of gases, admixing the gaseous components received from the pressurized supply tanks to form the gaseous blend, the producing a product output blend of the admixed gases. The system is also provided with means for venting gases from the system in the event of over pressurization, or leakage.

12 Claims, 7 Drawing Figures

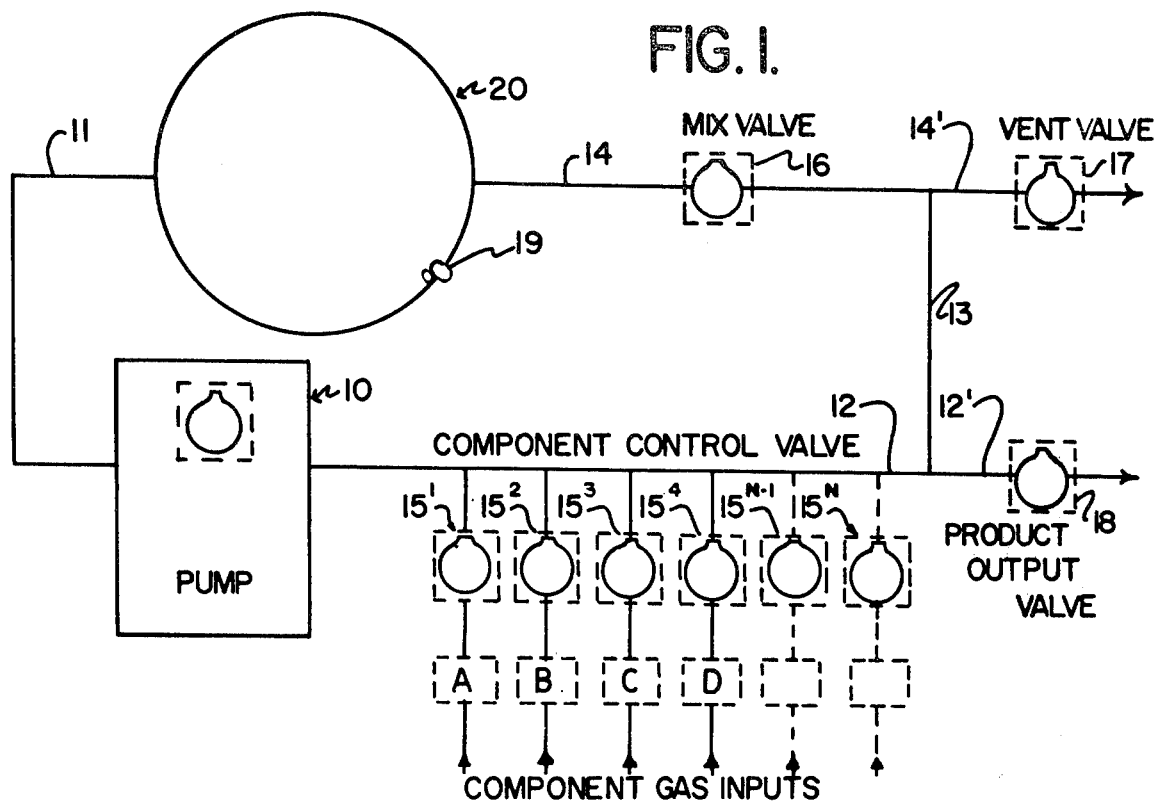
FIG. 1.
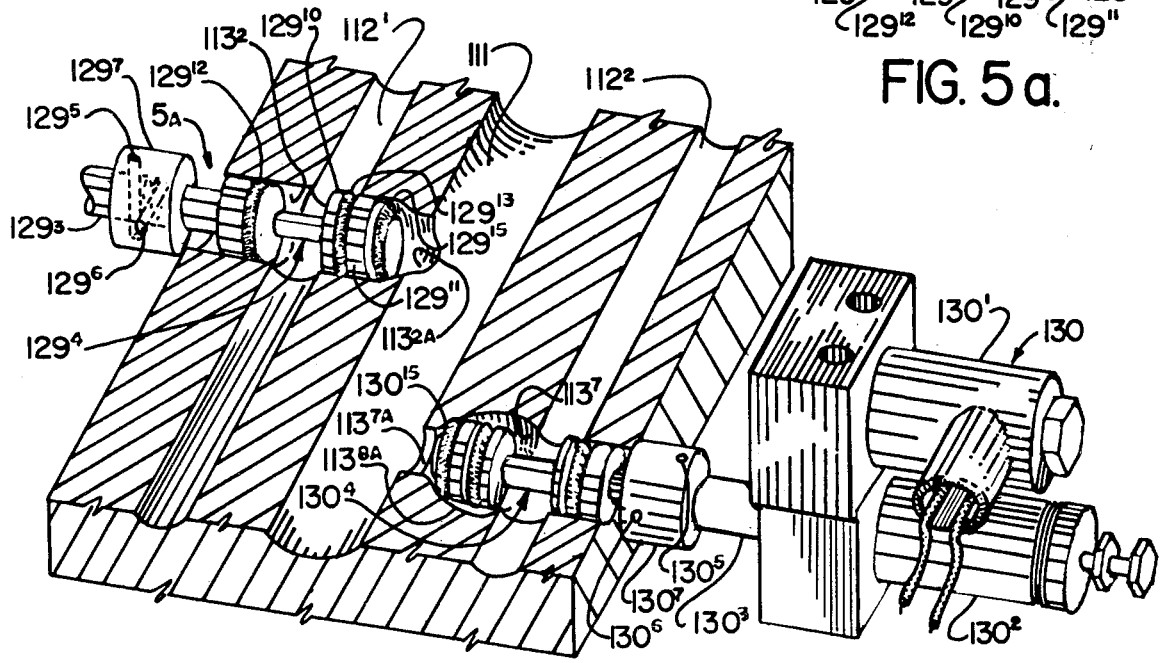
FIG. 5.
FIG. 5a.

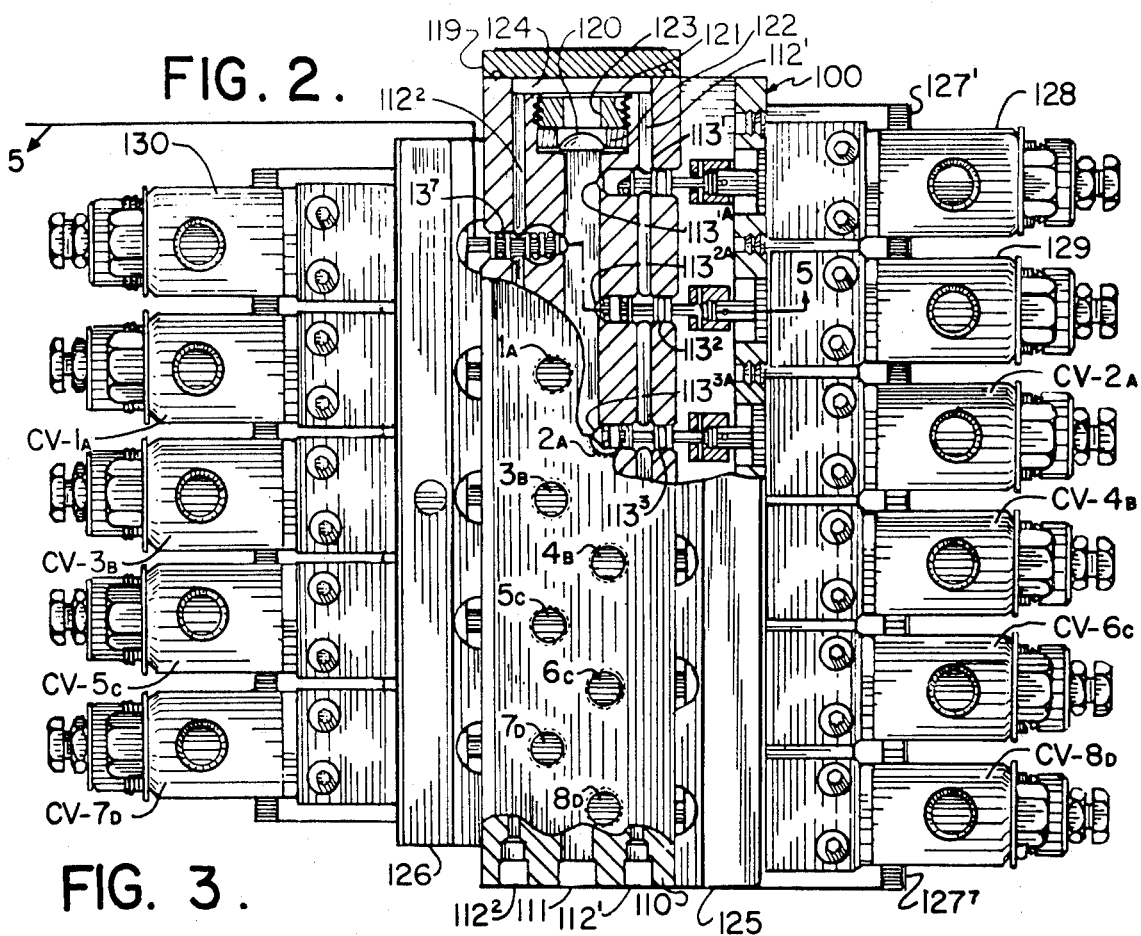
FIG. 2.
FIG. 3.
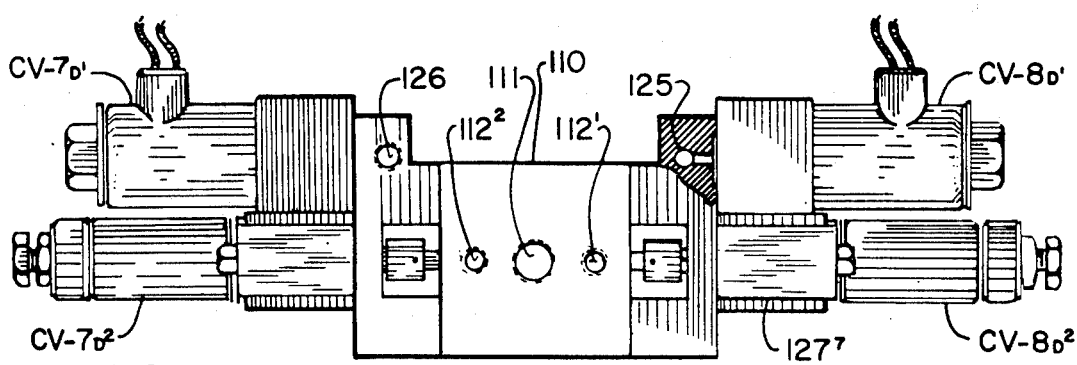
FIG. 4.
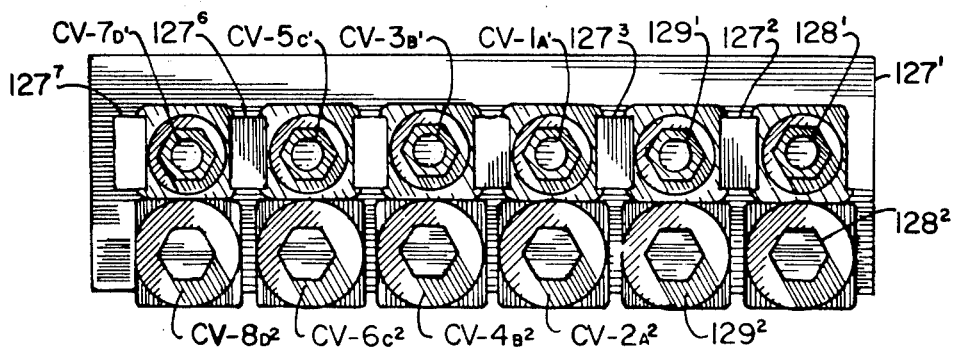

APPARATUS FOR PRODUCING CALIBRATION GASES SUITABLE FOR ANALYTICAL INSTRUMENTATION

RELATED APPLICATION

This application is generally related to application Ser. No. 698,883, by Donald P. Mayeaux, filed June 27, 1976, now U.S. Pat. No. 4,142,860, which issued Mar. 6, 1979. Said application is herewith fully incorporated by reference. Reference is also made to applications Ser. No. 006,665 by Donald P. Mayeaux filed of even data herewith.

The need for gaseous blends which contain accurately calibrated quantities of the component gases for use as reference gases in analytical instrumentation, and corresponding need for methods and apparatus for the production of such gaseous blends are well known. A background discussion of this need, and some of the problems associated with the production of gaseous blends is given in application Ser. No. 698,883, supra, at Pages 1-4. The application also cites various references, both patent and technical; and hence, it would not appear that any particularly useful purpose would be served by repetition.

It is worthy of note, however, that the partial pressure method of homogenizing, or admixing gases, has heretofore left much to be desired in providing an adequate method for the preparation of calibrated gas blends suitable as reference standards for modern analytical instruments, or for other industrial and research purposes. This deficiency occurs largely because the accuracy of the partial pressure method was quite limited due to the high pressures employed in blending the gases, the lack of a suitable means for homogenizing the gases, and the difficulties associated with heat changes produced during the blending operations. High pressures thus produce large compressibility factors, the extent of which are unpredictable with a sufficiently high degree of accuracy for producing accurate volumetric blends of an admixture of gaseous components, for real gases simply do not behave as the ideal gases of theoreticians; and such compositions are dependent on the state of the intermediate and final mixtures. Temperature variations have created many problems, and the decompression and compression of the gases constitutes a major source of error during blending. Consequently, the partial pressure method of blending gases has not been found to be a particularly suitable method for the preparation of highly accurately measured blends of gases, or calibration gases.

In U.S. Pat. No. 4,142,860 however, there is disclosed an apparatus for the production of calibrated blends of gases. The apparatus includes a pressurized vessel which forms a gas mixing chamber of large mass relative to the weight of the gaseous components blended therein, this unit serving to aid in the control of temperature fluctuations, and a movable stirring element is disposed within the vessel to homogenize the gases which are added to the vessel from a number of externally located pressurized tanks via a plurality of inlet valves mounted upon the tank. A pressure transducer measures the pressure of the gases in the gas mixing vessel, and an indicator displays the pressure reading. In operation, the mixing vessel can be purged, evacuated, the component gases added in seriatim, and the gases then stirred to produce a calibrated gas blend.

Whereas this apparatus has proven admirably staisfactory for blending gaseous components in accurately measured quantities there is yet room for further improvements. Among other things, e.g., a better means of homogenizing, or stirring the gases added to the mixing vessel is desired. Moreover, the necessity of having to mount a large number of valves and valve fittings directly on the mixing tank to eliminate dead volume leaves yet some possible margin of error in this regard, and in any event the elimination of dead volume by the necessity of mounting the several valves and valve fittings in this manner produces manufacturing and maintenance problems.

It is according a primary objective of the present invention to eliminate these and other disadvantages, particularly the well known disadvantages of the prior art.

A specific object is to provide apparatus and method for blending gaseous components in accurately measured quantities to provide calibration gas mixtures, especially a static gas blending system which can be readily automated.

Another, and more specific object, is to provide such gas blending apparatus which is of relatively simple and inexpensive construction, particularly one wherein the gaseous components can be added in preselected quantities, and the inputs readily monitored and controlled.

Another object is to provide a method for the production of a calibration, or reference gas, suitable for use in analytical instrumentation.

These objects and others are achieved in accordance with the present invention, an apparatus embodiment of which is constituted generally of a system which includes: a pressure vessel, or gas mixing vessel, preferably one of large mass, or of massive weight as relates to the volume of gaseous components capable of being mixed therein, a pressure transducer for measuring the pressure of the gases in said gas mixing vessel, or system, and producing an output signal in response to the measured pressure, a circulating pump connected in series via conduits with said gas mixing vessel, for homogenizing, or admixing, the gases, and a plurality of valve components, preferably a multi-component valve assembly operatively communicating the two ends of the conduits to form a circuit for flow, or circulation of gas therethrough, and through said system to provide the functions of purging gas from the system, admitting gaseous components received separately from pressurized supply tanks, admixing the gases to form a product gas blend, transferring all or some increment of said product gas blend from the system, and venting gases from the system.

The multicomponent valve assembly per se forms another apparatus embodiment, a preferred embodiment which in fact lies at the very heart of the system embodied by the preferred apparatus combination. The multicomponent valve assembly is comprised generally of a housing, preferably one within which is provided one or more vent passageways through which gases can be exhausted from the system, a component gas manifold within which gases can be injected and circulated through the system, and valve seats over which valves are mounted, the stem or plungers thereof intersecting a vent passageway and said component gas manifold. A mix valve, a product output valve, a vent valve, and a plurality of component gas valves, each of which can be independently opened and closed, particularly by signals independently received in programmed sequence from a computer, are mounted on said housing. Gases from the system are passed through said valve assembly in providing the functions of purging gas from the system, admixing the gaseous components received from pressurized supply tanks to form the gaseous blend, producing a product output blend of the admixed gases, and venting gases in the event of worn valves, or upset condition wherein too much pressure is generated in the system.

A preferred housing is one constituted of an elongate block in which there is provided parallel oriented, spaced apart axial passageways, each extending longitudinally through the block from an inlet at the same end of said block; a central passageway comprising a component gas manifold within which component gases of the blend can be injected, and circulated for admixing said gases, and preferably a plurality of vent passageways, suitably a pair of vent passageways, one located on each side of said central passageway and on a common plane therewith so that valves can be mounted on alternate sides of the block over valve seat openings formed by lateral openings in the block which connect a vent passageway with the component gas manifold. A plurality of valves which can be opened and closed in sequence, preferably by signals received in programmed sequence from a computer, are each mounted on a valve seat opening. Preferably, the valves are electrical or pneumatic, but more preferably a valve is constituted of both an electrical component and a pneumatic component. Suitably a single mix valve is employed, the mix valve forming an open-close or on-off connection in the circuit between the component gas manifold and the mixing vessel. A single product valve is also employed, this valve being mounted on said block over a valve seat opening adjacent a conduit which communicates the valve seat opening of said valve with a gas receiving source, or demand source external to said system. A single vent valve is mounted on said block over a valve seat opening, this valve being employed on an end of the component gas manifold, to minimize dead volume. An outlet communicates the component gas manifold via the orifice within the valve seat opening with a vent passageway. The block is also provided with a plurality of component gas valves. These are mounted on the block, each over a valve seat opening, and a gas inlet connected to each provides means for communicating a pressurized component gas supply tank for supply of a component gas. In closed position, the plunger of a valve can seal an orifice leading from said valve seat opening into said component gas manifold to close off the flow of a component gas from a supply tank into the component gas manifold, but in open position a component gas can be supplied by a pressurized supply tank to the component gas manifold. In a sequence of operation, the system can be purged in a cycle which includes opening the vent valve, closing all other valves, and then starting the pump to exhaust gas from the system, after which time the vent valve can be closed, the pump stopped, and a component valve opened to fill the system with a component gas, this cycle of exhausting and filling the system with the component gas being repeated a number of times to purge the system of all contaminants. After the system is exhausted of gas on the last step of the purging operation, the vent valve can then again be closed and each component gas can then be serially injeced into the system by sequentially opening and closing the respective component valve to inject the gases of the blend. And, on closing the component valve of the last gas to be added to the blend, the mix valve can be reopened, and the pump again turned on to circulate, mix and thoroughly homogenize the gaseous blend. The product output valve can then be opened to transfer the gas blend to the receiving source, or portions of the gas blend can be withdrawn as needed.

In a particularly preferred embodiment, the component gas valves are mounted on the housing, or block, in pairs, one valve of a pair being employed to inject a gaseous component at a rapid rate into the system, while the other valve of the pair is employed to inject additional increments of the same gaseous component into the system during blending. Generally, each valve of a pair is mounted on alternate sides of the housing, or block, and a pair of the component gas valves are employed for each component gas added to the system during blending. This permits fast initial injection of a relatively large volume of gas during blending with a first valve of the pair up to a preselected maximum pressure set point. As the gas then cools, and pressure drops to, or below, a minimum preset pressure level, additional smaller volumes or increments of the gas are added with a second valve of the pair. Each increment is added up to the maximum preselected pressure set point, until such time that the last increment is sufficiently small that the pressure virtually approximates or equals the maximum preselected set point after cooling.

The characteristics of a preferred gas blending system, multi-component valve assembly, and their principle of operation, as well as a method for the production of calibration gases will be more fully understood by reference to the following detailed description, and to the attached drawings to which reference is made on the subsequent description. Similar numbers are used in the different figures to represent similar components. Subscripts are used where there are a plurality of similar components, and where reference is made to a component without use of a subscript where a plurality of similar components are present, the reference is intended in the generic sense.

Referring to the drawings:

FIG. 1 shows an overview of a static gas blending system;

FIG. 2 depicts a preferred multi-component valve assembly;

FIG. 3 depicts a lower end view of said preferred multi-component valve assembly;

FIG. 4 depicts a right side view of said preferred multi-component valve assembly;

FIG. 5 depicts in section, and in isometric form, a Section 5—5 taken from FIG. 2;

Figure 6:
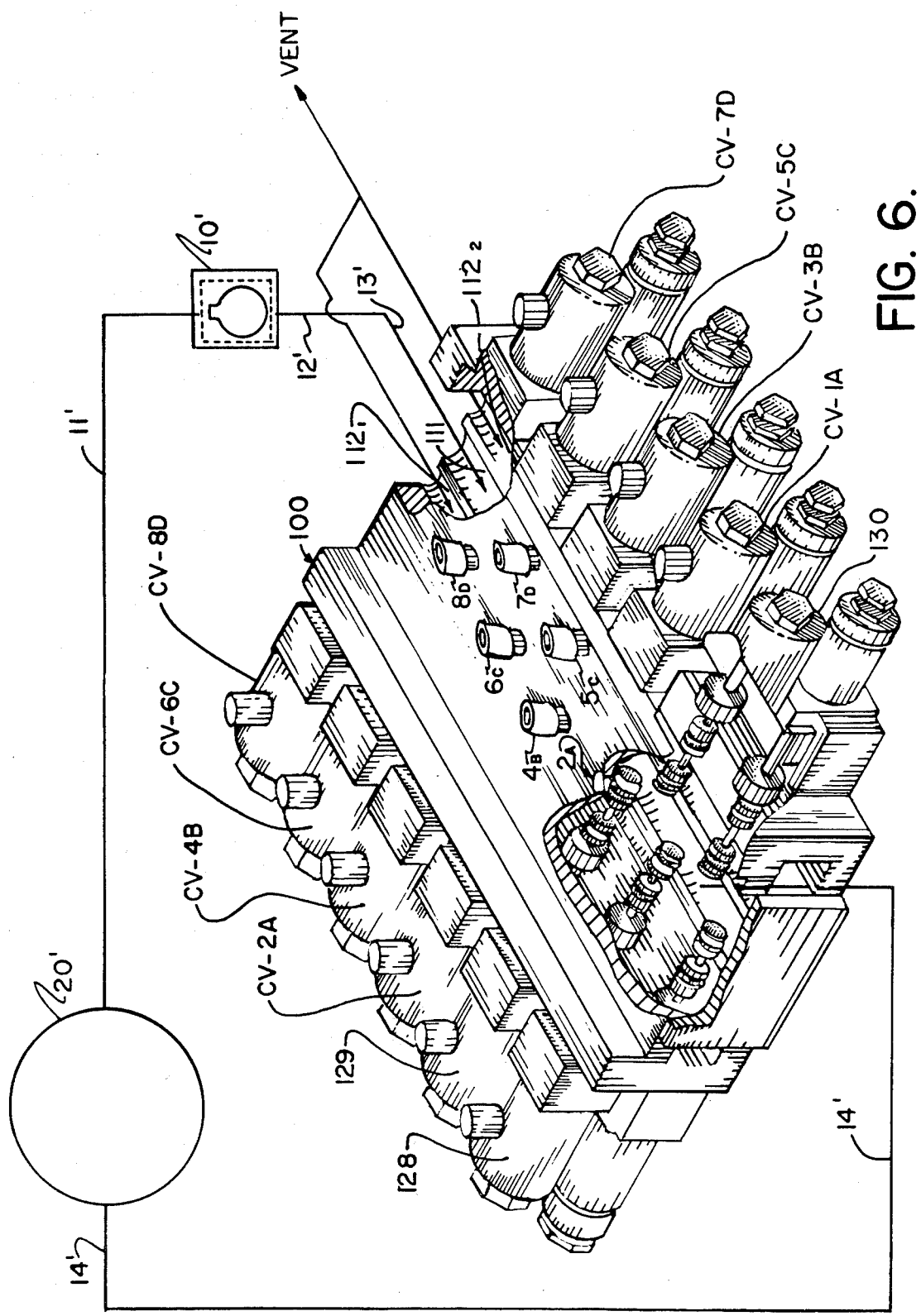

FIG. 5-A depicts a component, in partial section, taken from FIG. 5; and

FIG. 6 further depicts the multi-component valve of FIGS. 2-5 in combination with the static gas blending system.

Referring o FIG. 1 there is shown a digital static gas blending system which includes generally a pump 10, a vessel 20, suitably a massive spherical pressure vessel which is connected via line 11 to the pump 10, and communicating lines 12, 13, 14 which closes the circuit and serially connects the vessel 20 to the pump 10. The system includes a plurality of component control valves 15 ($15_{n-1}$ through $15_n$), each of which is connected to a different source of pressurized gas, for providing different gaseous components to the gas blending system. Thus, where four gaseous components are to be blended four component control valves are employed, e.g., component control valves $15_1$, $15_2$, $15_3$, $15_4$ to each of which is connected an individual tank of pressurized gas (not shown) and the gas is fed through the respective valve to line 12 of the digital static gas blending system. Three additional valves are required in the circuit, these comprising a mix valve 16 in line 14, a vent valve 17 located in line 14' which is a take off line between lines 13, 14, and a product output valve 18 located in line 12' which is a take off line between lines 12, 13. The system also includes an electrical absolute pressure transducer 19, or other suitable means, for accurately and continuously monitoring the absolute pressure within the vessel 20, the output of which is transmitted to a computer (not shown). It is preferably directly mounted within the body of the pressure vessel 20 to minimize the dead area between the pressure sensor of the transducer and the mixing chamber of said vessel 20. Suitable transducers for this usage are well known, and produced by various manufacturers in this country. Reference is made to U.S. Pat. Nos. 3,195,028; 3,271,669; and 3,318,153 for disclosures on the operation of pressure transducers, these patents being hereby incorporated by reference. Preferably, the output of the transducer which is in the preferred embodiment is a DC output voltage or current linear with pressure that is electrically communicated via electrical conduits to the computer. Each valve of the system is controlled by input signals from the computer in response to a predetermined program.

The pressure vessel 20 is necessarily one which provides a heat sink, or heat stabilizing means for rapid dissipation of the heat produced during the gas blending operation. The vessel might thus be one provided with a jacket within which a fluid can be passed in heat exchange relationship to the blended gases, or the vessel might be provided with various other heat exchange devices well known to the art. Suitably however, the vessel 20 is quite massive relative to the gaseous content introduced therein to provide a sufficient heat sink to hold the gas temperature substantially stable during the gas blending operation. Generally, the mass of the vessel 20 is at least about 20 pounds, and preferably ranges from about 30 pounds to about 42 pounds, for a vessel having an internal volume of 20 liters, the weight increasing proportionately as the internal volume of vessel 20 is increased. Suitably, the vessel 20 is of spherical shape and constituted of metal, e.g., stainless steel. In this system the pump 10 provides the required stirring for admixing the gases during blending, the heat being dissipated through the walls of the vessel 20.

In a typical gas blending operation, a gaseous blend can be formed from a plurality of gaseous components, e.g., inputs of gaseous components A, B, C, and D (from individually loaded pressurized tanks, not shown). The desired percentage composition of each of Components A, B, C and D within the total gaseous mixture to be blended is punched onto a keyboard as input to a computer, or other means, the computer controlling the several inputs of the gases to be blended by opening a valve in response to a predetermined pressure output from pressure transducer 19, a component being introduced into the line 12, of the previously purged system when the pressure within spherical vessel 20 is below a certain preselected minimum set-point, and the valve closed when the pressure within spherical tank 20 reaches a certain preselected maximum set point pressure. The gaseous components are then sequentially introduced into the previously purged system.

In an operating cycle, the method is one generally comprising the steps of purging the system, evacuating the system, introducing the component gases to the system, and then admixing or homogenizing the gases, after which time the blend is ready for transfer to the user as needed, or to a secondary vessel. In purging the system, notably the pressure vessel 20 which constitutes a mixing chamber, a first component gas, generally the largest component of the blend, is introduced to eliminate gas contaminates from the chamber; and then the vessel is evacuated of the purging gas and the pressure thereby reduced in the mixing chamber to a predetermined minimum level. A first component gas is then added to the pressure vessel 20, or mixing chamber, preferably sequentially in the order of the majority component first. Thus, if the concentration of four components of an admixture is $A>B>C>D$ in the final admixture, the gaseous components are introduced in the order A followed by B, B followed by C, and C followed by D; each addition of a gaseous component being completed before the next gaseous component is introduced. The first gaseous component is added in amount sufficient to increase the absolute pressure in the vessel, or mixing chamber, to a first predetermined level for the first gaseous component; the second gaseous component is then added to the vessel, or mixing chamber, in amount sufficient to increase the absolute pressure in the mixing chamber to a second predetermined level; a third component gas is then added to the vessel 20, or mixing chamber, in amount sufficient to increase the absolute pressure in the mixing chamber to a third predetermined level; and this addition sequence is continued up to the time of addition of the last gas which is to form a part of the component gas blend. The contents of the system are then circulated and stirred by starting and operating the pump 10 to obtain a homogeneous gas blend.

A typical cycle of operation employed in blending gaseous components A, B, C and D, supra, beginning with the step of purging the system is described by reference to FIG. 1 as follows:

(1) With mix valve 16, product output valve 18 and all of the component control valves 15 (i.e., $15_1$, $15_2$, $15_3$ and $15_4$) closed, and vent valve 17 open, pump 10 is energized to exhaust the contents of spherical vessel 20 via lines 11, 12, 13, 14' through the venting system. This done, and the pressure within spherical vessel 20 having reached a low preselected level, e.g., 5 pounds per square inch absolute (psia), or lower, vent valve 17 is then closed and pump 10 is cut off.

(2) Mix valve 16 is again opened. Valve $15_1$, to which is connected a pressurized tank (not shown) containing the gaseous component of the blend to be added in greatest concentration, is then opened. Gaseous Component A is then added up to a preselected pressure level, e.g., 15 to 50 psia. The gas fills the system by flow through lines 12, 13, 14; the gas flowing into line 11 after filling the vessel 20. Component control valve $15_1$ and mix valve 16 are then closed, vent valve 17 is then again opened, pump 10 is turned on and the contents of the system, especially vessel 20 are again vented by pumping the gas through lines 11, 12, 13, 14'. Vent valve 17 is again closed and valves 16 and $15_1$ are again opened to refill the system with gaseous component A. Mix valve 16 and component gas valve $15_1$ are then again closed, vent valve 17 is then opened and the gaseous contents of the vessel 20, and in fact the entire system, are again vented. The cycle of filling the system, and vessel 20 with Component Gas A, and thereafter purging vessel 20 of Component Gas A is conducted a plurality of times, usually about four times, until essentially all traces of any gaseous component other than gaseous Component A have been eliminated from the system. The purge thus completed, the system at low pressure, e.g., 5 psia, or lower, is now ready to receive the first permanent component of the blend, viz. gaseous Component A.

(3) With mix valve 16 open and valves 17, 18 and $15_2$, $15_3$, $15_4$ closed, valve $15_1$ is opened, and gaseous Component A flows through the system and into vessel 20 to fill with Component Gas A up to a first preselected pressure set-point level, e.g., 50 psia. The gas warms up slightly, and the pressure falls below the set point as the gas within the vessel cools. Continuous increments of gaseous Component A are added, the increments of Component A becoming smaller each time the set point is reached until such time that the last increment of gas maintains the preselected pressure set point level after the gas has cooled. On injection of the last increment of gaseous Component A into the system, and after thermal equilibrium has been reached, valve $15_1$ is closed.

(4) Valve $15_2$, with mix valve 16 open and valves 17, 18 and component gas valves $15_1$, $15_3$, $15_4$ closed, is opened and gaseous Component B is then added up to a second preselected pressure set-point level, e.g., 70 psi. On equilibration of the gas after the last increment of gaseous Component B is added, component gas valve $15_2$ is closed.

(5) With valves 17, 18 and component gas valves $15_1$, $15_2$ and $15_4$ closed, and mix valve 16 open, valve $15_3$ is opened and gaseous Component C is then added to the system up to a third preselected pressure set-point level, e.g., 80 psi. On equilibration of the gas after the last increment of gaseous Component C is added, component gas valve $15_3$ is closed.

(6) With valve 16 open, and valves 17, 18 and component gas valves $15_1$, $15_2$ and $15_3$ closed, valve $15_4$ is then opened and gaseous Component D is then added to the system up to a fourth set-point level, e.g., 85 psi. On equilibration of the gas after the last increment of gaseous Component D is added, component gas valve $15_4$ is then closed, pump 10 is turned on and the admixture of gaseous Components A, B, C and D is then circulated through the system until the stirred admixture is thoroughly homogeneous. The vessel 20 can serve as a storage facility or the admixture can be transferred to a storage vessel for subsequent use.

(7) Product valve 18, in the event transfer to a storage vessel is desired, is now opened and, with all of Component gas valves 15 and valves 16, 17 closed, the admixture of gases A, B, C and D is pumped from the system via lines 12, 12' as a product.

A liquid component, or components, can also be added to the vessel, or mixing chamber, in predetermined quantities as by injection of the liquid directly through a septum inlet (not shown) in the vessel; or directly injected through a component gas valve inlet. Within the mixing chamber the liquid is stirred and homogenized, or vaporized with the component gases. The liquid introduced into the mixing chamber forms a portion of the gaseous blend, and its volume can be related to the total volume of the gaseous blend by varying the pressure in the mixing chamber as described in U.S. Pat. No. 4,142,860, supra.

These gas blending functions, and others, are best conducted by use of a multi-component valve, or valve assembly, which includes a plurality of component control valve units, a mixing valve, a vent valve and a product output valve mounted within a single housing. A preferred valve of this character, a major advantage of which is that it can be located remote from the pressure vessel 20 itself, is described by reference to FIGS. 2 through 6.

Referring initially to FIGS. 2 through 4 there is depicted a preferred multi-component valve assembly 100 capable of carrying out all of the functions, and more, described by reference to FIG. 1. The multi-component valve assembly 100 is comprised generally of a unitary housing 110 on each alternate side of which is fitted two-way electro-mechanical valves which are controlled by inputs from a computer to open and close passageways within the housing 110 for carrying out the functions required in the aforesaid component gas blending operation. A mix valve, product output valve and a series of component gas valves equal in number to the maximum number of gaseous components that are to be blended together in admixture are located on one side of the valve housing. A vent valve is located at an end on the opposite side of the housing, along with a second series of component gas valves equal in number to the component gas valves located on the opposite side of the valve housing. One series of the component gas valves is employed to introduce relatively large volumes of the several gaseous components into the system, while the other series of valves are employed to introduce additional smaller increments of the gaseous components into the system. A pair of component gas valves, one valve of a pair being located on each side of the housing, is required for the introduction of each gaseous component to the system.

The housing 110 is constituted of an elongate solid block through the central axis, in the center of which is provided a central opening or passageway which serves as a component gas manifold 111. Vent passageways $112_1$, $112_2$, which traverse the length of the block, are located on each side of the component gas manifold 111, in line with, equidistant from and parallel to the gas manifold 111. A plurality of equidistantly spaced lateral openings 113 ($113_1$ through $113_6$ and $113_7$ through $113_{11}$, respectively), similar in size and shape, provide valve plunger seating surfaces which extend inwardly from the outer surface on each side of the block 110 (left and right side of FIG. 2) to intersect at right angle with a vent passageway $112_1$, or $112_2$, respectively, each opening being cut through the wall, providing a narrow passageway or orifice leading into the component gas manifold 111 wherein it terminates. A supply manifold, constituted of component gas inlet openings 1A, 2A, 3B, 4B, 5C, 6C, 7D, 8D, to which connections can be made for the introduction of component gases (e.g., component gases A, B, C, D of a blend, supra) from pressurized supply tanks into the component gas manifold 111, are located on the upper face of block 110 (FIG. 2), these openings extending into said laterally spaced openings $113_3$, $113_4$, $113_5$, $113_6$, $113_8$, $113_9$, $113_{10}$, $113_{11}$, respectively, at locations near the narrow passageways leading into the component gas manifold 111 such that a component gas from a source can be introduced therethrough into the gas manifold 111, or its flow interrupted by operation of a valve plunger, as subsequently detailed. A mix gas inlet connection located in block 111 above passageway $113_{1A}$ provides an inlet for input of gaseous components into the component gas manifold 111 when the plunger is raised for circulation of a gaseous component, or admixture of gaseous components to effect mixing, and a gas inlet connection located above passageway $113_{2A}$ provides an inlet into component gas manifold 111 for the removal of a gaseous product blend from the system. An oversized, or enlarged gas inlet connection located behind passageway $113_{7A}$, located near the end of passageway 111, provides an inlet from component gas manifold 111 into the vent passageway $112_2$ for venting gas from the system.

The vent passageways $112_1$, $112_2$, in addition to their function in normal operations also provide a unique safety feature in the event of a system upset, or malfunction which may develop excess pressure. Should, for any reason, too much pressure be developed for the system to handle, a rupture disk 120 is provided at the end of the block 110 (the upper end, FIG. 2) which, on being ruptured or broken leads into an open space or passageway 124 provided by an annular opening closed on one side by end wall 119. The passageway 124 is in open communication with vent passageways $112_1$, $112_2$. The rupture disk 120 is sombrero shaped, the peripheral edges thereof being fitted across the shoulders of a seating surface formed by an internally threaded enlarged opening 121 concentric with the component gas manifold 111 which it closes. It is held in place by an open centered washer 122 the inner edges of which, in turn, are pressed against the peripheral edges of the rupture disk 120 via tightening down on an externally threaded nut 123 which is threadably engaged via internal threads located within the opening 121. The rounded center of the rupture disk 120 is bulged outwardly and, on rupture at a preselected pressure which may be developed in the system, will pass gas via passageway 124 into vent passageways $112_1$, $112_2$. The vent passageways $112_1$, $112_2$ also provide a safety gas by-pass feature in the event that worn o-rings on the plunger produce leakage. This feature is particularly important in blending noxious gases, or gases of hazardous nature. In accordance with this embodiment, gases are prevented from escaping into the ambient atmosphere by maintaining the vent passageways $112_1$, $112_2$ at atmospheric pressure; this providing an easy escape route, or free access passageway for channeling an escaped gas, or gases, out of a working area to a safe storage, or disposal facility. In some instances the gases may be vented through a high stack, or chimney to the atmosphere.

The preferred valve components of the multi-component valve assembly 100 are each characterized as electro-mechanical valve units which can be activated in timed sequence by input signals received from the computer (not shown). The electrical valve component of an electro-mechanical valve unit permits a very rapid response to an electrical signal, the electrical valve component in turn being used to actuate a pneumatic valve component to provide a powered response for opening and closing a valve. Two-way valves, each comprised of a single electrical and single pneumatic component, are employed as controls for regulating the mixing, venting and product output functions. Generally similar valves are also employed in pairs, or as paired units for control of the component gas blending functions. In other words, a single two-way electro-mechanical valve unit is provided to control the gas mixing function, a single two-way electro-mechanical valve unit is provided to control the venting function, a single two-way electro-mechanical valve unit is employed to control the product output function, and a pair of two-way electro-mechanical valve units are employed to control each of the gaseous components which are introduced into the gas blending system. One electro-mechanical valve of a pair is employed to introduce a relatively large continuous volume of a single component gas into the system, especially as represented by the charges of the gas added to purge the system, or initial charge of a gas into the blending system during blending, and the second of the pair is employed to introduce relatively small increments of the same gas into the system at relatively rapid intervals during blending.

The several valves are stacked, or mounted side-by-side each atop a pressurized air, or gas manifold 125, 126, respectively, located on each side of block 110. Each valve is held securely in place via T-supports 127 ($127_1$–$127_{13}$) located at the terminal ends and in-between the pneumatic portion of an electro-mechanical valve unit (FIG. 4), the T-supports being bolted to the top of the gas manifolds 125, 126, respectively. The singly mounted two-way valves are identified as mixing valve 128 which is comprised of a pneumatic valve component $128_1$ and an electrical valve component $128_2$; a product output valve 129 which is comprised of a pneumatic valve component $129_1$ and an electrical valve component $129_2$; and a vent valve 130 which is comprised of a pneumatic valve component $130_1$ and an electrical valve component $130_2$. The paired sets of two-way component gas valves are, for convenience, identified by number and letter designations which characterize them in terms of the inlets of the supply manifold with which they are paired, and the component gases introduced therethrough, e.g., Component Gases A, B, C and D. Valves CV-1A, CV-3B, CV-5C and CV-7D mounted atop air manifold 126, each comprised of both an electrical valve component and a pneumatic valve component (designated in FIG. 4 by subscripts 1 and 2, respectively), are thus employed to inject relatively large volumes of component gases, e.g., gases A, B, C and D, respectively, into the component gas manifold 111, and valves CV-2A, CV-4B, CV-6C, and CV-8D, each also comprised of both an electrical valve component and a pneumatic valve component (designated in FIG. 4 by subscripts 1 and 2, respectively), are thus employed to inject relatively small increments of component gases, e.g., gases A, B, C and D, respectively, into component gas manifold 111 of block 110. The two valves of a paired set are identical in structure and function, the operation of one valve differing from the other of the pair only in the size of the orifice through which a component gas is admitted to the component gas manifold 111 from a pressurized tank; the valve of the pair which admits relatively large volumes of a gas being provided with a relatively large inlet opening to the component gas manifold 111, and conversely the valve which admits small increments of a gas bing provided with a small, or restricted inlet opening to the component gas manifold 111. In operation, the energizing of an electrical valve component by a signal from the computer (not shown) causes air from a manifold 125, 126, respectively, to be taken in through an opening in the bottom of an electrical valve component, the air in turn being transmitted through a passageway to the pneumatic valve component to actuate a piston which provides the power required to open and close the valve.

In a typical valve the electrical valve component is solenoid operated, an electrical energizing signal from the computer lifting a plunger which causes or permits the introduction of pressurized air therethrough into the pneumatically actuated valve component. The latter in turn may be suitably a single acting piston spring biased in closed position to provide a fail-safe feature in the event of a power failure, or other type of upset. Pressurized air fed into the pneumatic valve component thus positively forces the piston upwardly to uncover, or open an opening through which a component, is introduced, this action opening the valve. Conversely deenergizing the electrical valve component, or solenoid actuated valve can cut off the flow of air to the pneumatic valve component, let air escape from the valve via a suitable passageway to the atmosphere, and thereby permit the spring to return the pneumatic piston to a closed position. Electromechanical valve components of this type are well known and are available from various manufacturers.

The pressurized gas actuated pistons of the pneumatic valve components are affixed to valve stems, or to plungers, which are extended into the valve stem seats, or openings 113 of block 110 which, for convenience can be best illustrated by reference to FIGS. 5 and 5A. FIG. 5 shows vent valve 130, comprised of an electrical valve component $130_1$ and a pneumatic valve component $130_2$ upon the piston $130_3$ of which is affixed a valve stem, or plunger $130_4$. Additionally, FIG. 5 shows piston $129_3$ of the pneumatic valve component $129_2$ of product outlet valve 129 to which is affixed a plunger $129_4$. The valve stem, or plunger $129_4$, which is typical of all of the others, is shown in partial section in FIG. 5A. In either embodiment, suitably the plungers $129_4$ and $130_4$, respectively, are affixed to the piston $129_3$ and $130_3$, respectively, via attachment to enlarged tubular shaped coupling members $129_7$, and $130_7$, respectively, within which the perforated ends of pistons $129_3$ and $130_3$, respectively, are projected, the coupling members being provided with openings 90° apart through which pins $129_5$, $129_6$ and $130_5$, $130_6$, respectively, are projected to secure the plungers to each of the respective pistons.

A valve stem, or plunger, e.g., plunger $129_4$, is constituted of a relatively large perforated shank end through which a pin is passed to secure same to the tubular shaped coupling member $129_7$ and to piston $129_3$, and its middle and forward ends are provided with spaced apart concentrically projecting surfaces $129_8$, $129_9$ and $129_{10}$, $129_{11}$ between which seals, e.g., cup seals or o-rings, suitably o-rings $129_{12}$ and $129_{13}$ are mounted. The leading edge, or tip of the plunger is provided with a relatively small frusto-conic shaped projection $129_{14}$ within the small inwardly faced necked portion of which is seated a third oversized o-ring $129_{15}$, or one whose cross-sectional diameter is sufficient to provide a surface which extends or projects beyond the face of the member $129_{14}$. This design of the plunger permits the o-ring $129_{15}$ to be thrust downwardly tightly over a smaller diameter passageway, and seated to cover same and close, or prevent the passage of gas through said passageway. For example, when the plunger $129_4$ is activated and pressed inwardly toward component gas manifold 111, the o-ring $129_{15}$ is tightly seated over the passageway $113_{2A}$ to prevent escape of a product gas blend component gas manifold 111 through an opening (not shown) immediately over the projecting surface $129_{11}$, the diameter of which is restricted to cover only an area inside o-rings $129_{13}$, $129_{15}$. Conversely, when the plunger $129_4$ is lifted the o-ring $129_{15}$ is unseated, and o-ring $129_{15}$ is moved aside to uncover passageway $113_{2A}$ sufficiently to permit escape of gas through said opening (not shown), the gas flowing through passageway $113_{2A}$ from component gas manifold 111 to a source of use of the product gas blend. The o-ring $129_{13}$ located above o-ring $129_{15}$, on the other hand, prevents leakage and escape of gas which would introduce error into the system. The o-ring $129_{13}$, however, provides a safety feature in combination with vent passageway $112_1$ since gas which may by-pass o-ring $129_{13}$ enters passageway $112_1$ and is vented. The o-ring $129_{12}$, on the other hand, in view of its location, prevents escape of gas to the atmosphere, or valve exterior; the gas entering the vent passageway $112_1$. The design and function of all of the plungers of the valve assembly 100 are similar, inclusive of component gas valves CV-1A, CV-2A, CV-3A, CV-4A, CV-1B, CV-2B, CV-3B CV-4B and vent valve 130, although the function of the component gas valves is to inject a component gas from an external source into component gas manifold 111, and vent valve 130 is designed, in its normal function, to pass gases from component gas manifold 111 to vent passageway $112_2$.

The design of all of the component gas valves is, as suggested, similar to that of, e.g., product output valve 129. The operation of a component gas valve is also similar, e.g., as can be seen by reference to FIGS. 2 and 4, except that the lifting plunger on exposing opening 2A, which is communicated to a pressurized gas tank (not shown) containing gaseous Component A, the pressurized gas enters into the space between the two lowermost o-rings of the plunger of valve component CV-2A$_2$ and flows through the uncovered passageway $113_{3A}$ to enter into component gas manifold 111. The operation of the pneumatic component valve CV-1A$_2$ is similar in design and function to pneumatic component valve CV-2A$_2$ except that the opening 1A in the supply manifold from the pressurized tank which leads into opening $113_8$, and passageway $113_{8A}$ leading to component gas manifold 111 is more restricted to limit the amount of gas flowing into component gas manifold 111 given a finite period of time.

Though the function of the vent valve 130, as suggested, is to pass gas from the component gas manifold 111 to vent passageway $112_2$ the design of plunger $130_4$ need be no different from that of the other valve plungers. The function can be changed to provide for the flow of gas from component gas manifold 111 to vent passageway $112_2$ by providing an enlarged opening $113_{8A}$ (FIG. 5) sufficient to span and overcome the sealing effect normally provided by the o-ring immediately adjacent o-ring $130_{15}$ which closes the passageway $113_{7A}$; or by both providing said enlarged opening $113_{8A}$ and eliminating said o-ring immediately adjacent o-ring $130_{15}$. In operation of the vent valve 130 therefore, in its closed position shaft $130_4$ of the vent valve 130 is thrust inwardly, the o-ring $130_{15}$ being pressed tightly over the passageway $113_{7A}$ to close off flow between component gas manifold 111 and vent passageway $112_2$. On the lifting of the plunger $130_4$ the passageway $113_{7A}$ is uncovered and gas is passed from component gas manifold 111 therethrough via the enlarged opening 113₈ₐ to vent passageway 112₂.

The operation and function of multi-component valve assembly 100 is further depicted, in schematic fashion, by reference to FIG. 6. A typical cycle of operation stressing the function of said valve assembly 100 for the blending of gaseous components, beginning with the step of purging the system, is characterized as follows:

(1) With vent valve 130 open and all other valves closed (i.e., component gas valves CV-2A, CV-4B, CV-6C, CV-8D, CV-1A, CV-3B, CV-5C, CV-7D, mix valve 128 and product output valve 129) pum 10' is started and gas is withdrawn from sphere 20' via line 11' and injected into the component gas manifold 111 via lines 12', 13' and then exhausted through the passageway 113₇ₐ and vented through vent passageway 112₂ (FIG. 5).

(2) After the sphere 20' and entire system are exhausted, the vent valve 130 is then closed and mix valve 128 is opened. Component gas valve CV-1A is now opened, component gas A, the major gaseous component to be blended in the gaseous mixture, is then injected in relatively large amount per unit of time via opening 1A into component gas manifold 111, the gas passing through the mix valve 128 and line 14' to sphere 20'. Mix valve 128 is then again closed, vent valve 130 is then opened, pump 10' is started and the gaseous contents of the vessel 20', and system, are again vented. The cycle of filling vessel 20' with Component Gas A, and thereafter purging vessel 20 of Component Gas A is conducted several times until essentially all traces of a gaseous component other than Component A have been eliminated from the system. The purge thus completed, vent valve 130 is again closed. The system at low pressure, e.g., 5 psi, is now ready to receive the first component of the blend, viz. gaseous Component A.

(3) Mix valve 128 is again opened. Then valve CV-1A is opened and gaseous Component A is injected into component gas manifold 111, the gas flowing through mix valve 128 and line 14' into vessel 20' to fill same with Component Gas A up to the preselected pressure level, e.g., 50 psi. The gas warms up slightly and, on reaching the preselected preset pressure component gas valve CV-1A is closed. The gas cools, and the pressure in sphere 20' again drops below the preselected set-point. Gaseous Component A is then again added to the component gas manifold 11 via valve CV-2A again raising the pressure to the said preselected pressure level, e.g., 50 psi. Valve CV-2A is then again closed, the pressure falling below the set point as the gas within the vessel cools. Continuous increments of gaseous Component A are added via valve CV-2A, the increments of Component A becoming smaller as the preselected pressure set point is reached, until such time that the last increment of gas maintains the preselected set point level after the gas has cooled. Component control valve CV-2A is then closed.

(4-6) Component gases B, C and D are then sequentially added to the system via operation of valves CV-3B and CV-4B; valves CV-5C and CV-6C; and valves CV-7D and CV-8D, in their respective sequence. On equilibration of the gas after the last increment of gaseous Component D is added, component gas valve CV-8D is then closed, pump 10' is turned on, and the admixture of gaseous Components A, B, C and D then circulated through the system and sphere 20' until the admixture is thoroughly homogeneous; the admixture of gases being pumped by pump 10' via lines 12', 13' into the component gas manifold 111 of the valve assembly 100, the admixture passing through the open mix valve 128 via line 14' to sphere 20', and via line 11 back to pump 10' for recirculation. Pump 10, after complete homogenization of the gas blend, may then be shut off.

(7) Product valve 129 can now be opened and, with mix valve 128 open and all other valves closed, pump 10 can again be turned on to pump the admixture of gases A, B, C and D as a product.

It is apparent that various modifications and chages can be made in the apparatus, and method of practicing the present invention without departing from its spirit and scope. The static gas blending apparatus of this invention can be readily subjected to total automation, preselected quantities of the component gases of a blend being programmed on a computer and then, in response to signals from the computer, the components automatically blended, admixed and stored or transferred as a product output blend to a secondary vessel for subsequent use.

The various components of the apparatus is constructed of materials substantially inert or non-reactive to the chemical or corrosive action of the blended gases. The pressure vessel is preferably constructed of metals, e.g., ferrous metals such as iron, iron alloys, steel and the like; stainless steel being a preferred metal. The pump, and conduits are of conventional metals, and materials, as used in pump manufacture, as are the line and conduits. Whereas the valve body can be constructed of dense plastics, metals are also preferred, e.g., stainless steel. Conventional resilient or elastic-like materials are employed as seals.

It is apparent that various changes can be made in the apparatus, such as in the absolute or relative dimensions of the parts, materials used, and the like, or in the steps employed in carrying out the method, as will be apparent to those skilled in this art.

Precision is improved and time requirements for completion of a gas blend is reduced by temperature correction of the mixing chamber's absolute gas pressure. When temperature correction is applied, the vessel's mass requirements and temperature stabilization of the gas is less important. The gas temperature can be determined by a sensor located in the gas phase or by monitering the vessel wall temperature when low mass vessels are employed.

Having described the invention, what is claimed is:

1. A multicomponent valve assembly for use in a system for blending accurately measured predetermined quantities of gaseous components received directly from separate pressurized supply tanks, as on input signals received from a computer, the system including a mixing vessel, a pressure transducer associated with said vessel for measuring the pressure of the gases in said pressure vessel, producing an output signal in response to the measured pressure and transmitting same to said computer, and a circulating pump connected in a closed series via conduits which form a circuit, the multi-component valve assembly operatively communicating the two ends of the conduits for flow of gas therethrough in providing the functions of purging contaminants from the system, admixing the gaseous components received from the supply tanks to form the gaseous blend, producing a product output blend of the admixed gases, and venting gases from the system, which comprises:

a housing constituted of an elongate block within which is provided an axially oriented vent passageway extending longitudinally through the block to an inlet at the outer end of said block, through which gases can be vented from the system, a component gas manifold comprised of a passageway, axially oriented and parallel to said vent passageway, extending longitudinally from an inlet at the outer end of said block, within which component gases of the blend can be injected, and circulated for admixing said gases, a plurality of spaced apart valve seat openings, each extended from an inlet at the surface of said block laterally through said vent passageway to said component gas manifold to which it is communicated via an orifice leading into said component gas manifold, a mix valve which can be opened and closed as by signals received in programmed sequence from said computer, mounted on said block over a valve seat opening, an end of the conduit from said mixing vessel being communicated with said valve seat opening, the valve being sufficient to open and close the orifice leading from said valve seat opening into said component gas manifold to open or cut off communication with said mixing vessel via said conduit extended therefrom, a product output valve which can be opened and closed as by signals received in programmed sequence from said computer, mounted on said block over a valve seat opening which is communicated via a conduit with a gas receiving source external to said system, the valve being sufficient to open and close the orifice leading from said valve seat opening to said component gas manifold so as to open or cut off communication between said component gas manifold and said receiving source conduit, a vent valve which can be opened and closed as by signals received in programmed sequence from said computer, mounted on said block over a valve seat opening, and an outlet communicating the component gas manifold via the orifice within the valve seat opening with said vent passageway, the valve being sufficient to close the orifice of said valve seat opening to cut off communication between said component gas manifold and vent passageway or open said orifice and thereby open communication between said component gas manifold and vent passageway so that gas can be flowed freely through the component gas manifold, a plurality of component gas valves, each of which can be independently opened and closed as by signals received in programmed sequence from said computer mounted on said block each over a valve seat opening, to each adjacent valve seat opening of which is connected a gas inlet which provides means for communicating a component gas supply tank for supply of a component gas, each valve being sufficient to close the orifice leading from said valve seat opening into said component gas manifold to cut off the flow of a component gas from a supply tank into the component gas manifold, or open said valve seat orifice so that a component gas can be supplied by a supply tank to the component gas manifold, whereby the system can be purged in a cycle which includes opening the vent valve, closing all other valves, and then starting the pump to exhaust gas from the system, after which the pump can be stopped, the vent valve closed, and a component valve opened to provide the system with a component gas, this cycle being repeated a number of times to purge the system, and at the time the system is exhausted of gas on the last step of the cycle each component gas can be serially injected into the system by sequentially opening and closing the respective gas component valve to inject the gases of the blend and, on closing the component valve of the last gas to be added to the blend, the mix valve can be reopened, the pump again turned on to circulate, mix and thoroughly homogenize the gaseous blend, and the product output valve can then be opened to transfer the gas blend to a receiving source.

2. The apparatus of claim 1 wherein a vent passageway is provided on two or more sides of the elongate block, the component gas manifold is located deeper within the interior of the block, and valves are located on a plurality of the faces of the block.

3. The apparatus of claim 1 wherein a vent passageway is provided on alternate sides of the elongate block, the component gas manifold is located between the two vent passageways, and valves are located on alternate sides of the block.

4. The apparatus of claim 1 wherein a vent passageway is provided on alternate sides of the elongate block, and one each of a pair of component gas valves is located on alternate sides of the block for each component gas added, one valve of the pair being employed for the introduction of an initial large volume of a given component gas, the other being used for smaller volume additions of the gas.

5. The apparatus of claim 1 wherein an end of the component gas manifold is closed by a rupture disk which separates said component gas manifold from a passageway at the end of the block leading into said vent passageway, the rupture disk being one which ruptures at excessive pressure to vent gas from the component gas manifold into the vent passageway.

6. A multicomponent valve assembly for use in a system for blending accurately measured predetermined quantities of gaseous components received directly from separate pressurized supply tanks, as on input signals received from a computer, the system including a mixing vessel, a pressure transducer associated with said vessel for measuring the pressure of the gases in said pressure vessel, producing an output signal in response to the measured pressure and transmitting same to said computer, and a circulating pump connected in a closed series via conduits which form a circuit, the multi-component valve assembly operatively communicating the two ends of the conduits for flow of gas therethrough in providing the functions of purging contaminants from the system, admixing the gaseous components received from the supply tanks to form the gaseous blend, producing a product output blend of the admixed gases, and venting gases from the system, which comprises:

a housing constituted of an elongate block within which is provided
a pair of parallel aligned axially oriented vent passageways which extend from a passageway at one end of the block closed by an end wall, the vent passageways extending longitudinally through the block to an inlet at the other end of said block, through which gases can be vented from the system,
a component gas manifold comprised of a passageway, axially oriented, parallel to and located between said vent passageways, closed at the end leading into said passageway adjacent the closed end wall by a rupture disk through which gases can be vented to said vent passageways on rupture of the disk, the component gas manfold extending longitudinally to an inlet at the other end of said block, within which component gases of the blend can be injected, and circulated for admixing said gases,
a plurality of spaced apart valve seat openings on alternate sides of said block, each extended from an inlet at the surface of said block laterally through a vent passageway to said component gas manifold to which it is communicated via an orifice leading into said component gas manifold,
a mix valve which can be opened and closed as by signals received in programmed sequence from said computer, mounted on said block over a valve seat opening, an end of the conduit from said mixing vessel being communicated with said valve seat opening, the valve being provided with a plunger sufficient to open and close the orifice leading from said valve seat opening into said component gas manifold to open or cut off communication with said mixing vessel via said conduit extended therefrom,
a product output valve which can be opened and closed as by signals received in programmed sequence from said computer, mounted on said block over a valve seat opening which is communicated via a conduit with a gas receiving source external to said system, the valve being provided with a plunger sufficient to open and close the orifice leading from said valve seat opening to said component gas manifold so as to open or cut off communication between said component gas manifold and said receiving source conduit,
a vent valve which can be opened and closed as by signals received in programmed sequence from said computer, mounted on said block over a valve seat opening to said component gas manifold, and an outlet communicating the component gas manifold via the orifice within the valve seat opening with said vent passageway, the valve being provided with a plunger sufficient to close the orifice of said valve seat opening to cut off communication between said component gas manifold and vent passageway or open said orifice and thereby open communication between said component gas manifold and vent passageway so that gas can be flowed freely through the component gas manifold,
a plurality of component gas valves, each of which can be independently opened and closed as by signals received in programmed sequence from said computer, mounted on said block each over a valve seat opening, a pair of alternate valves being employed for each gas added, one valve of the pair being employed for the introduction of an initial large volume of a given component gas, the other being used for smaller additional increments of the gas during blending, to each adjacent valve seat opening of which is connected a gas inlet which provides means for communicating a component gas supply tank for supply of a component gas, each valve being provided with a plunger sufficient to close the orifice leading from said valve seat opening into said component gas manifold to cut off the flow of a component gas from a supply tank into the component gas manifold, or open said valve seat orifice so that a component gas can be supplied by a supply tank to the component gas manifold,
whereby the system can be purged in a cycle which includes opening the vent valve, closing all other valves, and then starting the pump to exhaust gas from the system, after which the pump can be stopped, the vent valve closed, and a component valve opened to provide the system with a component gas, this cycle being repeated a number of times to purge the system, and at the time the system is exhausted of gas on the last step of the purge cycle each component gas can be serially injected into the system by sequentially opening and closing the respective gas component valve, first the valve of a pair which introduces the large volume of a gas, and then the other of the pair to inject smaller additional increments of the gases of the blend and, on closing the component valve of the last gas to be added to the blend, the mix valve can be reopened, the pump again turned on to circulate, mix and thoroughly homogenize the gaseous blend, and if desired the product output valve can then be opened to transfer the gas blend to a receiving source.

7. In combination, apparatus for producing a calibration gas mixture of known composition from a plurality of component gases provided in pressurized tanks from which the gases are separately introduced and blended together to form a blend suitable for use in analytical instrumentation which comprises:
a pressure vessel which forms a gas mixing chamber sufficient to provide heat sink to hold the gas temperature substantially stable during the blending of the gases,
a pressure transducer associated with said vessel for measuring the pressure of the gases in said pressure vessel, and producing a usable output signal in response to the measured pressure,
a circulating pump connected via a conduit with said gas mixing vessel,
a mix valve connected via suitable conduits in line and in closed series with said pump and said pressure vessel, the pump providing a means for circulating gas, and homogenizing the mixture of gases introduced into said gas mixing chamber for substantially exhausting said gas mixing chamber when said mix valve is closed,
a multi-component valve assembly operatively communicating the two ends of the conduit for flow of gas therethrough, said multi-component valve assembly being comprised of
a housing constituted of an elongate block within which is provided
an axially oriented vent passageway extending longitudinally through the block to an inlet at the other end of said block, through which gases can be vented from the system, a component gas manifold comprised of a passageway, axially oriented and parallel to said vent passageway, extending longitudinally from an inlet at the other end of said block, within which component gases of the blend can be injected, and circulated for admixing said gases, a plurality of spaced apart valve seat openings, each extended from an inlet at the surface of said block laterally through said vent passageway to said component gas manifold to which it is communicated via an orifice leading into said component gas manifold, a mix valve mounted on said block over a valve seat opening, an end of the conduit from said mixing vessel being communicated with said valve seat opening, the valve being sufficient to open and close the orifice leading from said valve seat opening into said component gas manifold to open or cut off communication with said mixing vessel via said conduit extended therefrom, a product output valve mounted on said block over a valve seat opening which is communicated via a conduit with a gas receiving source external to said system, the valve being sufficient to open and close the orifice leading from said valve seat opening to said component gas manifold so as to open or cut off communication between said component gas manifold and said receiving source conduit, a vent valve mounted on said block over a valve seat opening, and an outlet communicating the component gas manifold via the orifice within the valve seat opening with said vent passageway, the valve being sufficient to close the orifice of said valve seat opening to cut off communication between said component gas manifold and vent passageway, or open said orifice and thereby open communication between said component gas manifold and vent passageway so that gas can be flowed freely through the component gas manifold, a plurality of component gas valves mounted on said block each over a valve seat opening, to each adjacent valve seat opening of which is connected a gas inlet which provides means for communicating a component gas supply tank for supply of a component gas, each valve being sufficient to close the orifice leading from said valve seat opening into said component gas manifold to cut off the flow of a component gas from a supply tank into the component gas manifold, or open said valve seat orifice so that a component gas can be supplied by a supply tank to the component gas manifold, whereby the apparatus can be purged in a cycle which includes opening the vent valve, closing all other valves, and then starting the pump to exhaust gas from the system, after which the pump can be stopped, the vent valve closed, and a component valve opened to provide a component gas, this cycle being repeated a number of times to purge the apparatus after which time the apparatus is exhausted of gas, and on the last step of the purge cycle each component gas can be serially injected into the apparatus by sequentially opening and closing the respective component valve to inject the gases of the blend and, on closing the component valve of the last gas to be added to the blend, the mix valve can be reopened, the pump again turned on to circulate, mix and thoroughly homogenize the gaseous blend, and the product output valve then opened to transfer the gas blend to a receiving source.

8. The apparatus of claim 7 wherein the mass of the pressure vessel is large relative to the mass of the gaseous contents introduced therein, and is at least 20 pounds for a vessel having an internal volume of 20 liters, the weight increasing proportionally for vessels having larger internal volumes.

9. The apparatus of claim 8 wherein the mass of the vessel ranges from about 30 pounds to about 42 pounds.

10. The apparatus of claim 7 wherein a vent passageway is provided on alternate sides of the elongate block, the component gas manifold is located between the two vent passageways, and valves are located on alternate sides of the block.

11. The apparatus of claim 7 wherein a vent passageway is provided on alternate sides of the elongate block, and one each of a pair of component gas valves is located on alternate side of the block for each component gas added one valve of the pair being employed for the introduction of an initial large volume of a given component gas, the other being used for smaller volume additions of the gas.

12. The apparatus of claim 7 wherein an end of the component gas manifold is closed by a rupture disk which separates said component gas manifold from a passageway leading into said vent passageway, the rupture disk being one which ruptures at excessive pressure to vent gas from the component gas manifold into the vent passageway.

* * * * *